(12) United States Patent
Purdy et al.

(10) Patent No.: US 7,422,740 B1
(45) Date of Patent: Sep. 9, 2008

(54) USE OF LYTIC TOXINS AND TOXIN CONJUGATES

(75) Inventors: Desmond Purdy, Salisbury (GB); Susan Charlton, Castle Cary (GB); Ian Henderson, Frederick, MD (US)

(73) Assignee: Health Protection Agency, Salisbury, Wiltshire (GB)

( * ) Notice: Subject to any disclaimer, the term of this patent is extended or adjusted under 35 U.S.C. 154(b) by 310 days.

(21) Appl. No.: 10/129,558

(22) PCT Filed: Nov. 13, 2000

(86) PCT No.: PCT/GB00/04329

§ 371 (c)(1),
(2), (4) Date: Nov. 12, 2003

(87) PCT Pub. No.: WO01/34205

PCT Pub. Date: May 17, 2001

(30) Foreign Application Priority Data

Nov. 12, 1999 (GB) .................................. 9926875.7

(51) Int. Cl.
A61K 39/395 (2006.01)
A61K 39/00 (2006.01)
(52) U.S. Cl. .................. 424/133.1; 424/133.1; 530/300
(58) Field of Classification Search ............. 424/178.1, 424/179.1, 183.1, 133.1
See application file for complete search history.

(56) References Cited

U.S. PATENT DOCUMENTS

| 4,340,535 | A | * | 7/1982 | Voisin et al. | ............. | 530/391.9 |
| 5,801,191 | A | * | 9/1998 | Bressi et al. | ................. | 514/449 |
| 5,973,116 | A | | 10/1999 | Espenetos et al. | | |
| 6,824,780 | B1 | | 11/2004 | Devaux et al. | | |

FOREIGN PATENT DOCUMENTS

| EP | 0815872 A2 * | 2/1998 |
| WO | WO 92/15327 | 9/1992 |
| WO | WO 94/21300 | 9/1994 |
| WO | WO 96/41608 | 12/1996 |
| WO | WO 97/33908 | 9/1997 |

OTHER PUBLICATIONS

Jang et al. (FEBS Letters 2004; 560: 81-85).*
Counis M.F. and Torriglia A. (Biochem. Cell Biol. 2000; 78: 405-414).*
Krishnamurthy et al. (Current Science 2000: 79; 1169-1181).*
Comayras et al. (Infection and Immunity 1997; 5088-5095).*
Kreitman (Curr Opin. Immunol. Oct. 1999; 11 (5): 570-578).*
Hinman, et al. A Membrane-Lytic Immunoconjugate Selective for Human Tumor T-Lymphocytes. International Journal of Immunopharmacology 20, pp. 467-478 (1998).
Jiang, et al. An Anti-CD19 Antibody Coupled to a Tetanus Toxin Peptide Induces Efficient Fas Ligand (FasL)-Medicated Cytotoxicity of a Transformed Human B Cell Line By Specific CD4+ T Cells. Clin. Exp. Immunol., vol. 114, pp. 173-178 (1998).
Beličič-Kolšek. An Immunotoxin Constructed by Conjugating Equinatoxin II, a Lethal and Cytolytic Polypeptide, to Immunoglobylin G+. Acta. Pharm., vol. 43, pp. 147-150 (1993).
Dunn, et al. Antigen Binding and Cytotoxic Properties of a Recombinant Immunotoxin Incorporating the Lytic Peptide, Melittin. Immunotechnology, vol. 2, pp. 229-240 (1996).
Kolonin, et al., Targeting Cyclin-Dependent Kinases in *Drosophila* With Peptide Aptamers. Proc. Natl. Acad. Sci, vol. 95, pp. 14266-14271, Nov. 1998.
Huang, et al., Activation of CDC 25 Phosphatase and CDC 2 Kinase Involved in GL331-Induced Apoptosis. Cancer Research 57, pp. 2974-2978, Jul. 1997.
Comayras, et al., *Escherichia coli* Cytolethal Distending Toxin Blocks the HeLa Cell Cycle at the $G_2/M$ Transition by Preventing cdc2 Protein Kinase Dephosphorylation and Activation. Infection and Immunity, vol. 65, No. 12, pp. 5088-5095, Dec. 1997.

* cited by examiner

*Primary Examiner*—Brandon J Fetterolf
(74) *Attorney, Agent, or Firm*—Hodgson Russ LLP

(57) ABSTRACT

Agents are provided which are capable of inhibiting the cell division cycle in a target cell of interest. The agents comprise first and second components, wherein the first component is a targeting moiety which is capable of directing the second component to the target cell of interest. The second component is capable of inhibiting the cell division cycle in the target cell of interest. The agents are preferably provided in the form of conjugates, and the second component is preferably a cytolethal distending toxin. Methods for the preparation of the agents, and the use thereof for treating proliferative cell disorders and intracellular pathogens are also provided.

4 Claims, No Drawings

SEQUENCE LISTING

<160> NUMBER OF SEQ ID NOS: 4

<210> SEQ ID NO 1
<211> LENGTH: 714
<212> TYPE: DNA
<213> ORGANISM: Escherichia coli

<400> SEQUENCE: 1

```
gtggataaaa aactaattgc atttttgtgc acacttataa ttactggttg ctcggatggg     60
atcggtgatt caccttcgcc accgggaaag aatgtagaat tagtcggaat tccagggcaa    120
ggtgtcgctg ttgcttcaaa tggcacatct ccaacatttg ggagcaacag tactgacttt    180
cctgatgttt caataatgag cacaggggga gcgatgctta ctgtttgggc cagacctgtc    240
cgtaactggc tttggggata tactccgttt gattcagtaa gttttggaga gaatcggaac    300
tggaaggttg tggatggtaa agatgccggt acagtgaaat ttgttaatgt tgcccagggg    360
acttgcatgg aggcctttaa aaacggggtg atacataata cctgtgatga taattcgtta    420
tctcaggagt ttcagttact gccttctact aatggtaatg tgcttataag aagtagtgcc    480
ttgcagacgt gtataagagc agactattta agcagaacta tactgtcacc gtttgctttt    540
acaatcaccc ttgagaagtg tcctggtgca aaagaagaaa cgcaagaaat gctatgggca    600
```

```
ataagtccac ctgtcagagc ggcaaaacca atctgatta aaccagaatt aagaccattc    660
agaccattgc caattccacc tcatgacaaa cctgatggaa tggagggagt atga         714
```

<210> SEQ ID NO 2
<211> LENGTH: 237
<212> TYPE: PRT
<213> ORGANISM: Escherichia coli

<400> SEQUENCE: 2

```
Val Asp Lys Lys Leu Ile Ala Phe Leu Cys Thr Leu Tyr Ile Thr Gly
  1               5                  10                  15

Cys Ser Asp Gly Ile Gly Asp Ser Pro Ser Pro Gly Lys Asn Val
             20                  25                  30

Glu Leu Val Gly Ile Pro Gly Gln Gly Val Ala Val Ala Ser Asn Gly
             35                  40                  45

Thr Ser Pro Thr Phe Gly Ser Asn Ser Thr Asp Phe Pro Asp Val Ser
         50                  55                  60

Ile Met Ser Thr Gly Gly Ala Met Leu Thr Val Trp Ala Arg Pro Val
 65                  70                  75                  80

Arg Asn Trp Leu Trp Gly Tyr Thr Pro Phe Asp Ser Val Ser Phe Gly
                 85                  90                  95

Glu Asn Arg Asn Trp Lys Val Val Asp Gly Lys Asp Ala Gly Thr Val
                100                 105                 110

Lys Phe Val Asn Val Ala Gln Gly Thr Cys Met Glu Ala Phe Lys Asn
                115                 120                 125

Gly Val Ile His Asn Thr Cys Asp Asp Asn Ser Leu Ser Gln Glu Phe
            130                 135                 140

Gln Leu Leu Pro Ser Thr Asn Gly Asn Val Leu Ile Arg Ser Ser Ala
145                 150                 155                 160

Leu Gln Thr Cys Ile Arg Ala Asp Tyr Leu Ser Arg Thr Ile Leu Ser
                165                 170                 175

Pro Phe Ala Phe Thr Ile Thr Leu Glu Lys Cys Pro Gly Ala Lys Glu
            180                 185                 190

Glu Thr Gln Glu Met Leu Trp Ala Ile Ser Pro Pro Val Arg Ala Ala
            195                 200                 205

Lys Pro Asn Leu Ile Lys Pro Glu Leu Arg Pro Phe Arg Pro Leu Pro
        210                 215                 220

Ile Pro Pro His Asp Lys Pro Asp Gly Met Glu Gly Val
225                 230                 235
```

<210> SEQ ID NO 3
<211> LENGTH: 822
<212> TYPE: DNA
<213> ORGANISM: Escherichia coli

<400> SEQUENCE: 3

```
atgaaaaaat tattattcct gttaatgatt ttgccgggta tttcttttgc agatttaagc    60
gactttaaag ttgcaacctg gaatttgcag ggctcaaatg caccgacaga aaataaatgg   120
aacacacatg ttcgacaact tgtcacggga agtggtgctg ttgatatcct gatggttcag   180
gaggctggtt caataccatc ttcagctaca ctaacggaac gtgaatttcg tacaccaggt   240
atcccaatga atgagtatat ctggaatact ggaacgaata gccgtccaca gcagcttttt   300
atttattttt cgcgaactga tgctctttct aatagagtaa atttagcgat agtatctaac   360
agaagagctg atgaggtgat tgtattatca cctccaacag tggcatcgcg tccgatcatt   420
```

```
ggaataagaa taggtaatga tgttttcttc tcaactcatg cattggcaaa ccgaggtata     480
gattctggag caattgttaa cagtgttttt gagtttttca acagacaaac agatcctata     540
agacaggccg ctaactggat gattgcagga gatttcaacc gttcacctgc tatgttattt     600
tcaacacttg agccgggaat ccgtaatcac gtgaatatta ttgcaccacc agatccaacg     660
caggccagtg gtggagtgct tgattatgct gtagttggaa actcagtgag ttttgtgctt     720
cccctgttga gggcttcgct gttatttggg ttgttaagag ggcaaattgc ctctgatcac     780
tttccggttg gcttcattcc cggaagagga gcaagaagat ga                       822
```

```
<210> SEQ ID NO 4
<211> LENGTH: 273
<212> TYPE: PRT
<213> ORGANISM: Escherichia coli

<400> SEQUENCE: 4

Met Lys Lys Leu Leu Phe Leu Leu Met Ile Leu Pro Gly Ile Ser Phe
  1               5                  10                  15

Ala Asp Leu Ser Asp Phe Lys Val Ala Thr Trp Asn Leu Gln Gly Ser
             20                  25                  30

Asn Ala Pro Thr Glu Asn Lys Trp Asn Thr His Val Arg Gln Leu Val
         35                  40                  45

Thr Gly Ser Gly Ala Val Asp Ile Leu Met Val Gln Glu Ala Gly Ser
     50                  55                  60

Ile Pro Ser Ser Ala Thr Leu Thr Glu Arg Glu Phe Arg Thr Pro Gly
 65                  70                  75                  80

Ile Pro Met Asn Glu Tyr Ile Trp Asn Thr Gly Thr Asn Ser Arg Pro
                 85                  90                  95

Gln Gln Leu Phe Ile Tyr Phe Ser Arg Thr Asp Ala Leu Ser Asn Arg
            100                 105                 110

Val Asn Leu Ala Ile Val Ser Asn Arg Arg Ala Asp Glu Val Ile Val
        115                 120                 125

Leu Ser Pro Pro Thr Val Ala Ser Arg Pro Ile Ile Gly Ile Arg Ile
    130                 135                 140

Gly Asn Asp Val Phe Phe Ser Thr His Ala Leu Ala Asn Arg Gly Ile
145                 150                 155                 160

Asp Ser Gly Ala Ile Val Asn Ser Val Phe Glu Phe Asn Arg Gln
                165                 170                 175

Thr Asp Pro Ile Arg Gln Ala Ala Asn Trp Met Ile Ala Gly Asp Phe
            180                 185                 190

Asn Arg Ser Pro Ala Met Leu Phe Ser Thr Leu Glu Pro Gly Ile Arg
        195                 200                 205

Asn His Val Asn Ile Ile Ala Pro Asp Pro Thr Gln Ala Ser Gly
    210                 215                 220

Gly Val Leu Asp Tyr Ala Val Val Gly Asn Ser Val Ser Phe Val Leu
225                 230                 235                 240

Pro Leu Leu Arg Ala Ser Leu Leu Phe Gly Leu Leu Arg Gly Gln Ile
                245                 250                 255

Ala Ser Asp His Phe Pro Val Gly Phe Ile Pro Gly Arg Gly Ala Arg
            260                 265                 270

Arg
```

USE OF LYTIC TOXINS AND TOXIN CONJUGATES

The present invention relates to toxin conjugates capable of effecting cell death, to methods for the preparation thereof, and to the use thereof for treating proliferative cell disorders and intracellular pathogens.

Conventional therapy systems utilise the cytopathic properties of toxin molecules to interfere with and halt cell metabolism. Several approaches have now advanced into clinical trials. Many of the generic problems associated with clinical administration of immunotoxins have been resolved allowing delivery of toxin in a safe and specific manner. An immunotoxin is a toxin conjugate comprising an antibody, or a part thereof, which has been coupled to a toxin molecule, or a part thereof having toxic activity. Immunotoxins made from intact toxins are outstandingly powerful cytotoxic agents for cells with appropriate antigens, often matching or even surpassing the potency of the native toxin in vitro (Franks, L. M. and Teich, N. M. Introduction to the Cellular and Molecular Biology of Cancer, second edition, Oxford University Press).

In the technical field of toxin conjugates there has been much research directed at "arming" antibodies so that they carry a cytotoxic moiety which will efficiently kill target cells. The cytotoxic moiety may, for example, be a bacterial toxin (such as diphtheria or pseudomonas toxin) or plant toxin (such as ricin or saporin), a chemical toxin, or a radioactive nuclide. Although simple in concept, there are several difficulties which must be overcome for this strategy to be effective. The conjugate must retain the capacity to recognise the target efficiently, it must gain access to the cell by endocytosis (since most of the toxic moieties which have been used act by inhibiting protein synthesis within the cell), and the linkage between the toxin and the antibody must be stable enough to withstand the passage through the body until it reaches the target cell. These difficulties are increased by the fact that the antibody-toxin conjugate itself may be immunogenic, and may provoke an immune response leading to its elimination. Thus far, only modest success has been achieved with therapies based on these conjugates [Nadler, L. (1990) Proc. Second Intl. Symp. Immunotoxins, pp. 58; and Byers, V. et al. (1990), 75, pp. 1426].

Many toxin conjugates have been well documented (see, for example, earlier patent applications by the present Applicant WO 96/33273 and WO 94/21300). Methods for preparing such toxin conjugates are well detailed in these patent applications and in the art [see also, for example, Brinkmann, U. (1996) Molecular Medicine Today, October pp. 439-446; Rathore D. (1996) Biochemical and Biophysical Res. Comm. 222 pp. 58-63; Rathore, D. et al. (1997) Gene 190, pp. 31-35; and Michael, N. P. et al. (1996) Immunotechnology 2, pp. 47-57].

A problem with conventional toxin conjugates is they have limited application in the treatment of conditions which result from intracellular abnormalities (eg. which may cause a cell to become cancerous). Accordingly there is a need for alternative agents for treating proliferative cell disorders such as leukemias, lymphomas and other related conditions.

In addition, conventional toxin conjugates have limited application against a large number of microorganisms which are capable of forming intracellular infections.

These include infections caused by species of *Salmonella, Yersinia, Shigella, Mycobacteria, Campylobacter* and *Chlamydia*. Live *Salmonella* and *Yersinia* can survive within the cells of mucosa of the gastrointestinal tract and fibroblasts, provide antigenic material continuously into the blood circulation and stimulate chronic inflammation and lead to arthritis. Other such infections are caused by the survival of *Legionella pneumophila* within alveolar macrophages and epithelial cells; the survival of *Listera monocytogenes* within cell cytosol; the intracellular protozoan *Toxoplasma gondii*; and the intracellular survival of *Bordetella* species (macrophages), *Staphylococcus aureus* (epithelial cells) and Group B streptococci (macrophages). Some of these infections are exclusively intracellular, others contain both intracellular and extracellular components. However, it is the intracellular survival cycle of bacterial infection which is suspected as a main supportive factor for disease progression.

Generally, these microorganisms do not circulate freely in the body, for example, in the bloodstream. Accordingly, intracellular microorganisms are often not amenable to drug treatment regimes. Where drugs are available, this problem has been exacerbated by the development of multiple drug resistant microorganisms. For similar reasons, vaccine therapies are not effective against such intracellular microorganisms. Also, increased systemic concentration of antibiotics to improve bioavailability within cells may result in severe side effects.

There is therefore a need for an agent capable of treating intracellular infections by microorganisms.

At least one of the above problems is alleviated by the present invention which provides pharmaceutical use of a toxin that inhibits the cell division cycle in a eukaryotic cell. The toxin is, for example, used in treatment of intracellular infections or proliferative cell disorders.

According to a first aspect of the present invention there is provided an agent comprising first and second components, the first component being a targeting moiety (TM) and the second component being capable of inhibiting the cell division cycle in a target cell of interest, wherein the TM is capable of directing the second component to the target cell of interest.

The first and second components may be physically associated with each other, for example by ionic charges, hydrogen bonds and/or Van der Waal's forces.

Alternatively, the first and second components may be chemically linked together, for example by a direct chemical bond, by a disulphide bridge, or by a linker molecule, thereby forming a conjugate.

The first and second components do not occur in nature together as an operative agent. For example, when the second component of the agent is a toxin molecule which exists in nature, the TM of the agent is something other than a bridging domain inherently present on the toxin molecule as it appears in nature. In one embodiment they are derived from different molecules. In another embodiment they are derived from different microbial sources, preferably from different bacterial phlya, genera, or species.

The term "conjugate" in the context of this invention also includes a fusion protein of the first and second components. One embodiment is an immunotoxin. A "conjugate" is a molecule which does not occur in nature.

In contrast to toxin conjugates in the prior art which exert their effects on cell membranes thereby causing lysis of the target cell, or by inhibition of protein synthesis, the agents of the present preferably exert their effect by inhibiting or even blocking the cell division cycle in a target cell.

In one embodiment, the agent is capable of inhibiting mitosis and/or is capable of acting on the actin cytoskeleton in the target cell of interest.

It is preferred that the agent causes release of at least some of the cellular contents of the target cell so that the host's immune system may then invoke an inflammatory reaction against the released cellular contents.

In one embodiment, the agent causes cell death to the target cell of interest, thereby effecting potential release of all cellular contents.

In use, it has been observed that the agent of the present invention may cause vacuolation in a target cell of interest.

In a preferred embodiment, the agent is capable of causing cell death by a "lytic mechanism" in certain cell-types such as epithelial cells (eg. HeLa, HEp-2, and Vero cells).

The term "lytic mechanism" describes a mode of cell death which is principally effected by the second component on a target cell and includes: transport of the second component across the cell membrane; necrosis; and non-apoptosis. The feature common of these modes of cell death is that a target cell is caused to lyse (ie. burst or break), and that the cellular contents are then released. The "lytic mechanism" of cell death does not substantially inhibit protein synthesis in the target cell. In particular, a target cell is caused to distend to such an extent that cell lysis occurs once the elastic limit of the target cell has been surpassed. Thus, the cellular contents of the target cell may be forcibly released as the cell swells under the influence of the toxin or agent of the present invention. The host's immune system may then invoke an inflammatory reaction against the released cellular contents.

One potential drawback associated with use of conventional bacterial or plant toxins is that such toxins cause cell death in a non-inflammatory manner by apoptosis. Apoptosis is the term given to the sequence of events: programmed cell death induced by various means (including some cancer chemotherapeutics, radiation, tumour necrosis factors, and diphtheria and pseudomonas toxins); and spontaneous absorption of any released cellular contents. Cellular contents released during apoptosis may be absorbed by surrounding cells and may not therefore be optimally exposed to the host's immune system [see Fraser, A. and Evan, G. (1996) Cell, 85, pp. 781-784]. Thus, a "lytic mechanism" of cell death may help to elicit an optimal inflammatory response against the released cellular contents.

It is an advantage of the present invention that in certain circumstances cellular contents released by toxins or agents or other compositions of the invention are more readily recognisable by a host's immune system.

The term "targeting moiety" (TM) means any structure which is capable of binding to the target cell of interest.

In one embodiment, the TM is capable of functionally interacting with the binding site causing a physical association between the TM and the target cell. Examples of suitable TMs include an antibody or fragment thereof, a receptor capable of binding to a ligand on the cell of interest, and a ligand (eg. a sugar, a peptide, a transferrin molecule) capable of binding to a receptor on the cell of interest.

Preferably, the TM is an antibody, or a fragment thereof, for a cell-surface epitope. The resulting agent, wherein the TM and second component are conjugated together, is called an immunoconjugate, or immunotoxin.

The TM need not demonstrate 100% specificity for the cell of interest, though naturally a degree of specificity is desirable for a highly efficient system.

The TM per se may be capable of both binding and translocation. An example of such a TM is the sugar molecule galactose [see Plank, C. et al. (1992), Bioconjug. Chem. 3(6) pp. 533-539 and Freidinger, R. M. et al. (1989), Trends Pharmacol. Sci. 10(7), pp. 270-274]. Alternatively, the TM may be capable of binding, but not translocation.

Some preferred TMs and potential target cells/binding sites are illustrated below.

| TM | Target |
|---|---|
| MFE-23 | carcinoembryonic antigen |
| αLMP | Latent membrane proteins (leukaemias) |
| αCD22 | CD22 (B cell malignancies) |
| BR96 | Lewis$^y$-related antigen (lung, breast, colon carcinomas) |

The term "binding" includes any interaction between the TM and the target cell of interest which permits the second component to be delivered into the target cell. This delivery process is one in which at least the cell division cycle inhibiting activity of the second component enters the target cell of interest. The TM may become separated from the second component during this delivery process.

The term "translocation" refers to passage of at least the second component from the outside of a target cell of interest to the inside (ie. the cytosol) of the target cell of interest, where it may then exert its cell division cycle inhibiting activity. Once taken into the target cell of interest by endocytosis the second component must then leave the resulting endosome across the endosomal membrane to enter the cytosol. The ability to achieve specific cell binding and entry of toxin molecules into the cytosol has been well documented in the literature [for example: Pastan, I., Willingham, M. C., & Fitzgerald, D. S. P (1986) Cell 47, pp. 641-648; Olsnes, S., Sandvig, K., Petersen, O. W. & Van Dews, B. (1989) Immunol. Today 10, pp. 291-295; Strom, T. B., Anderson, P. L., Rubin-Kelley, V. E., Williams, D. P., Kiyokawa, T. & Murphy, J. R. (1991) Ann. N.Y. Acad. Sci. 636, pp. 233-250].

A preferred source of the "translocation" function is the component which forms the second component of the present invention. A particularly preferred source is a cytolethal distending toxin (CDT). This particular group of toxin molecules in discussed in more detail below.

The "translocation" function may be provided by an alternative source, for example from a Clostridial neurotoxin (see WO 94/21300), Pseudomonas Exotoxin A [Prior, T. I. et al. (1992) Biochemistry 31, 14, pp. 3555-35559], or a diphtheria toxin [London, E. (1992) Biochimica et Biophysica Acta 1113, pp. 25-51], or from a non-toxin source, for example, haemagglutinin of influenza virus [Murata, M. et al. (1992), 31 (7), pp. 1986-1992].

Any one second component may be coupled to one or more TMs. Where a given second component is coupled to more than one TM, each such TM may bind to a different cell-type. Alternatively, each TM preferably binds to the same cell-type, although each may recognise a different site on the same cell-type.

The second component of the present invention is capable of inhibiting the cell division cycle in a target cell suitably for treating intracellular infections or proliferative cell disorders. The target cell is preferably a eukaryotic cell.

In one embodiment, the second component inhibits mitosis in a target cell, suitably for treating intracellular infections or proliferative cell disorders. In another embodiment, the second component causes cell death by distention of the target cell without substantially inhibiting protein synthesis in the target cell.

The second component may be derived from a number of different sources such as cytolethal distending toxin (CDT), bacterial toxins which act on the actin cytoskeleton of a cell, and DNases. The second component preferably inhibits activation of p34$^{cdc2}$ protein kinase and/or the cyclin B1 complex. Alternatively, or in addition, the second component may inhibit cdc25 phosphatase, which phosphatase is considered responsible for the activation of p34$^{cdc2}$ protein kinase and/or cyclin B1 complex.

An example of a bacterial toxin which acts on the actin cytoskeleton of a cell is *Clostridium botulinum* C2 toxin [see Barth, H. et al. (1999) Infection and Immunity, October 1999, vol. 67, No. 10, pp. 5083-5090]. This toxin, more preferably at least the enzymically active portion of C2, may be employed as the second component in the present invention.

In another embodiment, the second component may be a DNase. Suitable DNases include, for example: NUC-18; DNase I; DNase II; Ca$^{2+}$-independent DNase; and nuc-1 [see Peitsch, M. C. et al (1994) Trends in Cell Biology, vol. 4, February, pp 37-41 for a comprehensive review of DNases]. In a preferred embodiment, the second component has a DNase I activity.

The second component is preferably a cytolethal distending toxin (CDT), whereas the first component is preferably not derived from CDT. The CDT may be associated with or may possess a DNase activity, preferably a DNase I activity.

CDTs make up a newly-described class of protein cytotoxins produced by an increasing number of identified bacteria, for example, bacteria of the genera *Campylobacter, Shigella, Haemophilus* and *Actinobacillus* and several *E. coli* species. This newly-described class of cytotoxins are genetically similar and have an approximate maximum sequence variation of up to 57%. CDTs are typically heat sensitive (70° C., 15 minutes), trypsin sensitive, and non-dialysable proteins. CDTs are chacterised by a mode of action which involves the blocking of the eukaryotic cell cycle.

The morphological changes associated with CDT action are characteristic in certain cells and are distinct from those observed with other bacterial toxins. Cloning and sequencing of genes encoding CDT from various sources have confirmed that CDT is a unique toxin unlike other previously described bacterial toxins. There are some similarities between CDT and cytotoxic necrotizing factor (CNF), but while CNF causes limited cell enlargement and a general multinucleation in Chinese hamster ovary cells, CDT-induced cell distension is more striking and only limited multinucleation is observed [see Aragon, et al. (1997) Infection and Immunity, 65 (9), pp. 3774-3780]. A further distinction between CDT and CNF is that CNF causes cell death by apoptosis and not by a lytic mechanism which facilitates a host cell to invoke an optimal inflammatory response to the released cellular contents.

To date, the following CDTs have been cloned and partial or complete nucleotide sequences have been published:

*Escherichia coli* E6468/62 [see Scott, D. A. and Kapar, J. B. (1994). Infect. Immun. 62: 244-251)];

*E. coli* 9142-88 [see Pickett, C. L. et al. (1994) Infection and Immunity, pp. 1046-1051];

*E. coli* 1404 [Peres, S. Y. et al. (1997). Mol. Microbiol. 24: 1095-1107];

*Campylobacter jejuni* 81-176 [see Pickett, C. L. et al. (1996) Infection and Immunity, pp. 2070-2078];

*Haemophilus ducreyi* 35000 [Cope, L. D., et al. (1997). Proc. Natl. Acad. Sci. USA. 94: 4056-4061];

*Shigella dysenteriae* 144 [Okuda, J., et al. (1995). Microb. Pathog. 18: 167-172]; and

*Actinobacillus actinomycetemcomitans* FDC Y4 [Mayer, M. P. A. (1999). Infect. Immun. 67: 1227-1237].

Novel, Cdt A nucleic acid (SEQ ID NO.1) and peptide sequences (SEQ ID NO.2 are presented in the present application, derived from *E. coli* UKR77. Corresponding novel sequences for Cdt B are presented as SEQ ID No.3 (nucleic acid) and SEQ ID No.4 (peptide) from, the same *E. coli* strain.

CDT production by other *E. coli* strains and *Campylobacter* and *Shigella* species has been described, and further sequence information is imminent. Additional sequence data are provided in: Pickett, C. L. et al. (1996) Infection and Immunity, pp 2070-2078; and Shenker, B. J. et al. (1999) J. Immunol; pp 4773-4780.

The above bacteria represent preferred sources of CDT according to the present invention. The particularly preferred source is *E. coli* or *Campylobacter*.

CDT is encoded by three genes, designated cdtA, cdtB and cdtC which are arranged in an apparent operon. These three genes encode polypeptides with predictable or apparent molecular masses of approximately 25-35 kDa (cdtA), 28-30 kDa (cdtB), and 20-21 kDa (cdtC)—see Aragon, V. et al. (1997), Infection and Immunity, 65 (9), pp. 3774-3780.

In *Campylobacter jejuni* the cdt genes are organised with four base pair overlaps between the stop codons and translation start codons of cdtA and cdtB. There is a ten base pair gap between the cdtB and cdtC genes.

Any one CDT subunit may be employed in an agent according to the present invention. The preferred sub-unit is the gene product of cdtB or cdtC. Alternatively, two or more sub-units may be employed.

Reference to CDT throughout this specification is to be understood as reference to the CDT holotoxin, or to a sub-unit of the CDT holotoxin (eg. the gene product of cdtA, cdtB, or cdtC), optionally including the native leader sequence, which is capable of inhibiting the cell division cycle in a target cell. In a preferred embodiment, CDT possesses a cell distending property, is capable of causing cell death by a lytic mechanism, and/or is capable of blocking mitosis in a target cell of interest, particularly in epithelial cells (eg. HeLa cells). The term CDT also includes a fragment, variant or derivative of the holotoxin or a sub-unit thereof, with or without a leader sequence, which possesses one or more of the above properties.

CDTs appear to have a mode of action which involves blocking of the cell cycle in $G_2$ phase, immediately prior to initiation of mitosis. CDTs have been shown to institute a $G_2/M$ phase block in the cell cycle [see Comayras, C. et al. (1997) Infection and Immunity, 65 (9), pp. 5088-5095; and Peres, S. Y. (1997) Mol. Microbiol., 24 (5) pp. 1095-1107]. This irreversibly blocks cell division, thus preventing proliferation of toxin treated cells. Cell death occurs within 3-5 days, during which time cells continue to synthesise cellular proteins and grow, causing, in at least certain cell types (eg. epithelial cells), a characteristic swelling, eventual cell rupture and release of cellular components.

This mitotic block has been shown to arise from the action of the toxin on a specific cyclin-dependent kinase. Cyclin-dependent kinases and their associated cyclin regulatory units govern the transition of all eukaryotic cells into mitosis. CDT is thought to act by preventing dephosphorylation of the cdc2 protein kinase which forms a complex with cyclin B1. The dephosphorylation of this complex is the trigger to initiate mitosis. CDT appears to block removal of a phosphate group from a specific tyrosine residue by cdc25-phosphatase, thus leaving cdc2 in the inactive tyrosine phosphorylated form and thereby preventing normal progression through the cell cycle. However, it is presently unclear if this irreversible phosphorylation of cdc2 is a direct result of some physiological effect by the toxin on this molecule itself, or the cdc25-phosphatase (or its regulatory cascade) which is responsible for dephosphorylation of the cdc2/cyclin B1 complex. These data have been generated from the *E. coli* and *C. jejuni* CDTs [see Comayras, C. et al. (1997); Peres, S. Y. (1997); and Whitehouse, C. et al. (1998). Infection and Immunity 66: 1934-1940-discussed above].

Similar findings have recently been described for the *A. actinomycetemcomitans* and *H. ducreyi* enzymes (Abst No: A35 Cortes-Bratti, X et al., and Abst. No: B27 Shenker, B. J. et al., 9th European Workshop on Bacterial Protein Toxins, Ste Maxime, France, 1999).

Following treatment of a cell with an agent according to the present invention, in one embodiment, the mean length of a target cell is typically increased by at least 3-fold that of normal cells, and preferably by up to 5- to 7-fold that of normal cells. Treated cells are typically mononucleated and the mean diameter of a nucleus is typically at least 2-fold of that of normal cells. However, not all potential target cells (eg. CDT-sensitive cells) display equivalent cell distention before cell death occurs (see Pickett and Whitehouse (1999) Trends in Micobiol. 7: 292-297).

Native CDT may exhibit a degree of binding specificity for epithelial cells. It is preferred that any residual specificity, especially for epithelial cells, is minimised in the CDT conjugates according to the present invention. This may be achieved by removal or partial removal of the native TM, leaving only the catalytic function and translocation function (see Lemichez, E. et al. (1997) Mol. Microbiol. 24: 1061-1070.

Similarly, second components other than CDT may have a degree of native binding specificity. In one embodiment, such native binding specificity is removed or diminished.

Since native CDT demonstrates a residual binding affinity for epithelial cells, in a separate aspect of the present invention CDT per se may be employed as a TM for drug delivery purposes, in which case the distending activity of the toxin is preferably minimized or removed.

CDT also demonstrates a cell internalisation ability. This translocation function of CDTs may be employed for drug delivery purposes. Again, the distending, and optionally the residual binding affinity, would be preferably minimized or removed.

The toxin, preferably CDT, and/or agents of the present invention may be added to a pharmaceutically acceptable carrier and/or diluent (eg. sodium chloride) to form a pharmaceutical composition.

According to a preferred embodiment, the present invention provides a toxin conjugate capable of effecting cell death by a lytic mechanism, comprising: a cytolethal distending toxin (CDT); and a targeting moiety (TM) coupled thereto. The TM comprises a ligand to a cell-surface binding site present on a cell of interest, and is capable of functionally interacting with the binding site causing a physical association between the TM and the cell. The toxin conjugate forms a molecule which is capable of introducing the CDT, or the subunit thereof, into the cytosol of the cell, thereby causing distention of the cell followed by lysis and release of cellular contents.

According to a second aspect of the present invention, there is provided a method of preparing an agent, comprising coupling together as a first component a Targeting Moiety (TM), and a second component which is capable of inhibiting the cell division cycle in a target cell.

A number of basic methods for preparing toxin conjugates are known in the art. These include: Brinkmann, U. (1996) Molecular Medicine Today, October pp. 439-446; Rathore D. (1996) Biochemical and Biophysical Res. Comm. 222 pp. 58-63; Rathore, D. et al. (1997) Gene 190, pp. 31-35; and Michael, N. P. et al. (1996) Immunotechnology 2, pp. 47-57.

Any of the above basic methods may be employed to produce a conjugate according to the present invention, and Examples are given below.

The second component (eg. CDT) and the TM may be prepared separately, prior to coupling, by recombinant means as detailed below.

The TM may be coupled to any part of the second component (eg. CDT). The coupling between the TM and the second component should preferably not impair the binding of the TM to the cell membrane binding site, or affect the activity of the second component.

The selected TM preferably demonstrates conformational stability. The coupling process preferably places the TM at a distance from the second component sufficient to provide the TM with a degree of rotational flexibility so as to preserve maximum interaction of the TM with its receptor. This may be achieved, for example, by use of a short peptide linker sequence.

Examples of suitable spacer molecules include

PPPIEGR [Kim, J. S., Raines, R. T. (1993). Ribonuclease S-peptide as a carrier in fusion proteins. Protein Sci 2(3): 348-56];

collagen-like spacer [Rock, F., Everett, M., Klein, M. (1992). Over-expression and structure-function analysis of a bioengineered IL-2/IL-6 chimeric lymphokine. Protein Eng 5(6):583-91];

trypsin sensitive diphtheria toxin peptide [O'Hare, M., Brown, A. N., Hussain, K., Gebhardt, A., Watson, G., Roberts, L. M., Vitetta, E. S., Thorpe, P. E., Lord, J. M. (1990). Cytotoxicity of a recombinant ricin-A-chain fusion protein containing a proteolytically-cleavable spacer sequence. FEBS Lett October 29; 273(1-2):200-4]; and N-succinimidyl 3-(2-pyridyldithio) proprionate (SPDP) [see, for example, WO94/21300].

Alternatively, the TM may be chemically coupled directly to the second component (eg. CDT), for example, by combined use of iodoacetamide to block free sulphydryl groups but retain free amino groups on one component, and EDAC (1-ethyl-3-[3-dimethylaminopropyl]carbodiimide hydrochloride) to activate carboxy groups on the second component, followed by covalent coupling of the two components via an amide bond.

A preferred means for chemical linkage is heterofunctional crosslinking via a disulfide bridge.

One embodiment is first to introduce free sulfhydril groups (—SH) in the TM molecule which may not have such groups in its native state. This can be done, for example, by thiolation of one or more free aminogroups on the TM with a reagent (eg. 2-iminothiolane) which modifies these groups and introduces —SH groups at these positions (this leads to TM-SH). By changing the ratio of TM to 2-iminothiolane, temperature and pH of the reaction, modification can be achieved that will not impair TM binding to its receptor. Preferably 1-2 SH groups per TM molecule are so modified. Then modified TM is purified from the low molecular weight reagent by gel filtration, for example a Sephadex G-50 column and concentrated to about 1-3 mg/ml over a microfiltration membrane with a 30 kDa cut-off.

The second component (eg. CDT) is pre-treated by mixing with a hetero-bifunctional cross-linking agent (eg. Sulfo-SMCC, sulphosuccinilimidyl 4-(N-maleimidomethyl)-cyclohexane-1-carboxylate) which covalently binds to free —$NH_2$ groups on the second component, leaving second component molecules in the solution having active maleimide groups which are able to react with a —SH group from the thiolated TM. The degree of second component modification may be controlled by the ratio of the crosslinking agent to second component. At the end of the reaction, conjugate is isolated from the reaction mixture by gel filtration on Sepharose 6B column and concentrated by membrane filtration.

Another strategy of developing TM-S-S-linker-second component product can involve the activation of TM free —NH$_2$ groups and cross-linking activated TM with —SH groups at the second component surface. The outcome of this process depends on the availability and accessibility of —SH groups at the second component's surface.

According to a third aspect of the present invention, there is provided a recombinant method for preparing a conjugate according to the present invention, comprising expression of one or more nucleic acid constructs encoding a TM and the second component (eg. toxin).

Preferably, the teaching of Michael, N. P., et al. (1996) is to be followed, which illustrates a schematic diagram of a complete immunotoxin construct. Following Michael, N. P., et al. (1996), second component (eg. CDT) may be substituted into the construct in place of the carboxypeptidase coding sequence, thus translationally fusing the second component and TM component of the conjugate.

Alternatively, the nucleic acid constructs encoding the second component and TM may be operably linked such that transcription and translation results in an assembled conjugate. This latter embodiment may be achieved by following the general methodologies detailed in Brinkmann, U. (1996) Molecular Medicine Today, October pp. 442-443. Chemical derivatisation may also be utilised to link the second component and TM in the assembled conjugate.

Preparation of a transgenic second component (eg. CDT) is ordinarily carried out by polymerase chain reaction (PCR) amplification of DNA from published sequences of genes encoding CDT. Nucleotide primers are extended to generate full length second component genes (eg. holotoxin or subfragments of toxin genes), depending on specific requirements. Amplified products are typically cloned into non-toxic *E coli* K12 strains using plasmid-based systems, which also facilitate the simple nucleotide sequence analysis of the cloned PCR products. If required, these amplified PCR products (eg. encoding full length or subfragments of CDT) can then be cloned into an appropriate plasmid expression system to generate protein products.

A specific method for preparation of an assembled transgenic CDT conjugate is described in Example 2.

According to a fourth aspect of the present invention there is provided a method for the treatment of a proliferative cell disorder, comprising administering a toxin that inhibits the cell division cycle in a target cell, such as by administering an agent (eg. a CDT conjugate) of the present invention.

Proliferative cell disorders may be associated with the presence of certain epitopes expressed on the surface of cells. Alternatively, proliferative cell disorders may be associated with the presence of certain epitopes which are over-expressed in comparison with the same cell-type in a non-diseased state. Such epitopes present a means for targeting an agent of the present invention to these cells.

By specifically targeting an agent to a cell displaying an undesirable disease pathology it is possible to disrupt cellular function and bring benefit for the patient.

The agents of the present invention may be employed for the treatment of a whole range of proliferative disorders. Of interest is the treatment of leukemias, lymphomas and other related conditions.

Of particular interest are Epstein Barr virus (EBV) induced Burkitts lymphoma, Hodgkins lymphoma and post-transplantation lymphoproliferative disease which are often difficult to treat. Also of interest is the treatment of other proliferative skin disorders such as melanomas and psoriasis, and diseases with poor $CD4^+$ responses which present surface specific antigens.

Current therapeutic regimens combine radiation and chemotherapy, but in patients with recurrent or refractory B-cell disease these regimens have a disease-free survival of less than 30%. This area of therapy forms the principle therapeutic outlet for the conjugates and/or agents of the present invention. Further research will identify additional disease candidates.

Delivery is preferably in the form of an injectable composition, applied either directly into the site of disease or intravenously/intramuscularly in cases of systemic illness. Also, depending on the disease being treated, it may be preferable to topically apply therapeutics to the skin surface, such as may be the case in the treatment of proliferative skin diseases such as psoriasis. Similarly, if specific gastric complaints are to be treated using toxin based therapy, an oral delivery route may be more appropriate.

The agent of the present invention may be administered at a concentration of approximately 3000 enzyme units per $m^2$ of patient body surface area. The agent is preferably diluted in 0.9% sodium chloride. The agent is preferably administered as an injectable formulation, but may also be administered, for example, topically.

According to a fifth aspect of the present invention there is provided a method for treating an infection caused by an intracellular pathogen, comprising administering a toxin that inhibits the cell division cycle in a target cell, such as by administering an agent (eg. a CDT conjugate) of the present invention. These include infections caused by *Salmonella, Yersinia, Shigella, Campylobacter* and *Chlamydia*. Live *Salmonella* and *Yersinia* can survive within the cells of mucosa of the gastrointestinal tract and fibroblasts, provide antigenic material continuously into the blood circulation and stimulate chronic inflammation and lead to arthritis. Also infections caused by the survival of *Legionella pneumophila* within alveolar macrophages and epithelial cells; infections caused by the survival of *Listeria monocytogenes* within cell cytosol; infections caused by an intracellular protozoan *Toxoplasma gondii*; and infections caused by the intracellular survival of *Bordetella* species (macrophages). *Staphylococcus aureus* (epithelial cells) and Group B streptococci (macrophages). Some of these infections are exclusively intracellular, others contain both intracellular and extracellular components. However, it is the intracellular survival of bacterial infection which is suspected as a main supportive factor for disease progression.

The present invention is also applicable for suppression of intracellular persistence within macrophages of other bacteria such as *Leishmania donovani, Legionella pneumophila, Bordetella pertussis* and other species of bordetellae, Group B streptococci, *Salmonella* species, *Chlamydia* and *Borrelia burgdorferi*.

The preferred inflammatory mechanism of cell death of the present invention potentially exposes intracellular pathogens to the immune system, which may then stimulate antibody production against these pathogens.

Cells infected by a particular pathogen often express epitopes not expressed by the same cell-type in an uninfected state. An example of this is antigen presenting cells of the immune system such as B-cells, infected with Epstein-Barr virus in leukaemic conditions. Selection of a specific TM directed to such epitopes allows the second component (eg. CDT) to be targeted to infected cells, which then become distended and lyse. This releases the intracellular pathogen which becomes exposed to the host's immune system.

Alternatively, should an intracellular pathogen infect a certain cell-type within a localised area of a patient, local administration at the site of infection with a toxin that inhibits the cell division cycle in a target cell, such as an agent of the present invention having a TM directed to that cell-type may be adequate for treatment purposes.

The present invention is therefore particularly advantageous for the treatment of disease in which the disease-causing pathogen's intracellular growth effectively prevents detection by the immune system. Such treatment may be coordinated with a drug regime (eg. an antibiotic) directed against the pathogen.

Induction of an effective host immune response against a pathogen subsequently reduces the necessity for repeated immunotoxin therapy, making therapies cheaper and far less likely to elicit an immune response in their own right, which is often a major problem associated with repeated immunotoxin therapy.

The preferred delivery means and dosage details for treating an intracellular pathogen are as described above for the treatment of proliferative cell disorders.

According to a sixth aspect of the present invention there is provided a pharmaceutical composition, comprising a toxin capable of inhibiting the cell division cycle in a target cell, such as an agent according to the present invention, and a pharmaceutically acceptable salt, diluent and/or carrier. The toxin is preferably CDT.

Residual binding affinity of the toxin (in the case of CDT, epithelial cell affinity) is preferably removed or reduced. Specific targeting of the toxin or component thereof is not essential because the composition may be administered locally to the area of infection and delivery of the toxin or component thereof to the target cell/s may be achieved by random endocytosis. A TM is not therefore required with this aspect. According to this aspect, the toxin may be, for example, injected directly into a target site, for example, a tumour.

According to this aspect of the present invention there is also provided use of a toxin capable of inhibiting the cell division cycle in a target cell, such as an agent according to the present invention, in the manufacture of a medicament for the treatment of a proliferative cell disorder or for the treatment of an intracellular pathogen. The toxin is preferably CDT.

According to a seventh aspect, the present invention provides a method of stimulating and/or enhancing an immune response preferably against an intracellular pathogen, comprising administering a toxin capable of inhibiting the cell division cycle in a target cell, such as an agent according to the present invention, to a patient. An advantage of this method is that there is a reduced need for repeated administration to counter a particular intracellular infection and/or proliferative cell disorder.

According to this aspect, there is also provided use of a toxin capable of inhibiting the cell division cycle in a target cell, such as an agent according to the present invention, in the manufacture of a medicament for stimulating and/or enhancing an immune response, preferably against an intracellular pathogen.

EXAMPLES

Example 1

In Vitro Expression of cdt::gfp Fusions

Subfragments of the cdtABC operon, encoding cdtA, cdtB and cdtC genes lacking their signal peptides were amplified by PCR from C. jejuni 81-176 DNA template using primers based on the published nucleotide sequence. Restriction sites were added to flanking coding sequences, locating BglII sites flanking the cdtA and cdtC genes and BamHI recognition sequences flanking the cdtB gene (due to the presence of a BglII site within the cdtB coding sequence). Amplification products from PCR reactions were cloned into pCR2.1TOPO (Invitrogen) and sequenced to confirm no errors existed in the coding sequence. DNA encoding the truncated cdtA, cdtB and cdtC genes was then subcloned into pEGFP (Clontech) at the BglII site, thus fusing these genes in frame with the C-terminal of EGFP, encoding a red-shifted GFP (green fluorescent protein) variant optimised for higher expression in mammalian cells.

Plasmids were recovered from E. coli clones and packaged into activated dendrimers using the Qiagen Superfect Transfection reagent. Packaged DNA was used to transform semi-confluent HeLa cells in 24-well plates, according to the manufacturers instructions (Qiagen). After 24 hours incubation, some cytopathic effects were noted on cell lines transfected with plasmid and also in negative controls exposed to transfection reagent only. However, in cells exposed to plasmid, successful transfection was indicated by weak cytosolic green fluorescence. No fluorescence was detectable in transfection reagent only treated wells. Transfection ratios of HeLa monolayers were approximately 1-2% for cdtA, cdtB and cdtC transfections. Often cells expressing GFP were rounded in appearance, although similarly rounded cells were visible in wells exposed to transfection reagent alone, indicating that CPE could not necessarily be ascribed to CDT induced effects.

Example 2

Modification of DEPT (Directed Enzyme Prodrug Therapy) System to Incorporate CDT Subfragments The generation of MFE-23::CPG$_2$ fusion proteins has been previously described by Michael N. P., et al. (1996). This construct utilises a single-chain variable antibody fragment (scFv), designated MFE-23, derived from a phage display library and which is reactive against carcinoembryonic antigen (CEA). CEA is overexpressed on the surface of specific tumours. This is either directly fused, or by means of peptide linker, to carboxypeptidase G$_2$ (CPG$_2$) which acts to convert a non-toxic prodrug to a toxic drug at the tumour site, greatly facilitating the specific destruction of cancer cells.

A similar antibody fusion may be generated utilising the well characterised MFE-23 antibody fragment (or similar), substituting the CPG$_2$ moiety with the gene encoding the catalytically active cdt subfragment in order to generate a model system for proof or principle experiments. Protein may be expressed in *Escherichia coli* expression systems in an unglycosylated form, or in a glycosylated form in *Pichia pastoris*. In *E. coli* expression systems, the MFE-23::CPG$_2$ fusion is preceded with the pelB signal peptide to ensure export to the periplasm. The lac promoter controls expression of the fusion protein.

Appropriate recognised eukaryotic transcriptional control sequences and protein export signals are substituted in the *P. pastoris* expression system.

Fusion protein expressed in *E. coli* systems has been shown to effectively localise in nude mice bearing human tumour xenografts, giving favourable tumour to blood ratios following the administration of 2.8 μg [$^{-125}$I] CPG2::MFE-23 per mouse (Michael N. P., et al. 1996).

Example 3

Cloning and Expression of CDT from *E. coli* (or a Sub-Unit Thereof) Using Fusion Protein Technology Standard molecular biology protocols were used for all genetic manipulations (e.g. Sambrook et al. 1989, Molecular Cloning a Laboratory Manual, Second Edition, Cold Spring Harbor Laboratory Press, Cold Spring Harbor, N.Y.). The CDT operon of (and individual genes thereof) of *E. coli* UKR-77 and 92-1799 were amplified by PCR. PCR primers were designed to have homology to published CDTI and II sequences (Scott, D. A. and Kaper, J. B. 1994, Infection and Immunity 62:244-251; Pickett, C. L., Cottle, D. L., Pesci, E. C. and Bikah, G. 1994. Infection and Immunity 62:1046-1051), and to incorporate restriction enzyme sites to facilitate cloning and sub-cloning of the PCR products. PCR products were cloned into the vector pCR2.1TOPO (Invitrogen) as described by the manufacturer. Novel *E. coli* CDT sequences are described in FIG. 1. After sequence verification the CDT genes (individually) were cloned into the expression vector pET43a (Novagen), replacing the BamH1-Xho1 or EcoR1-Xho1 fragments. The ligations were transformed into the expression hosts BL21 (DE3) RIL (Stratagene) or AD494 (DE3).

Additional sequences for adding affinity purification tags and one or more specific protease sites for the subsequent removal of these affinity tags were also included in the reading frame of the gene products. The recombinant proteins expressed in the pET43a purification system were produced with carboxy-terminal 6× histidine tags to facilitate purification and amino-terminal NusA tags to facilitate expression of the CDT gene products in a soluble form.

Briefly, cultures of *E. coli* BL21 (DE3) RIL pET43a-cdtA, B or C were grown in L-broth-ampicillin (100 µgml$^{-1}$) to an OD$_{600}$ nm of 2.5-3.8, and protein expression was induced by the addition of 1 mM IPTG for approximately 2 h.

Fusion proteins were located in the insoluble fractions of the cell extract after cell lysis using Bugbuster protein extraction reagent (Invitrogen). The insoluble material was washed with NaCl containing solutions and fusion proteins obtained after washing in diluted Bugbuster solutions.

Example 4

Cloning and Expression of CDT from *C. jejuni* (or a Sub-Unit Thereof) Using Fusion Protein Technology CDT genes were amplified from *C. jejuni* 81-176B genomic DNA using PCR, essentially as described in example two. After cloning the PCR products into pCR2.1TOPO, the sequence verified CDT genes were subcloned into pMALc2x (NEB), replacing a BamH1-Xba1 fragment; or pET43a (Novagen) replacing a BamH1-Xho1 fragment.

The recombinant proteins expressed in pMAL (using a method essentially as in example 2) were produced with amino-terminal maltose-binding protein tags allowing proteins to be purified by affinity chromatography on amylose resin. Factor Xa protease sites were included within the protein for subsequent removal of these purification tags. Cells were lysed using Bugbuster protein extraction reagent (Novagen) and lysates cleared by centrifugation. Fusion proteins were present in the insoluble fraction of the cell extract. They were purified from inclusion bodies using the Novagen Protein Refolding kit. All buffers used were as specified by the manufacturer.

Example 5

Formation of Targeting Moiety (TM)-CDT Conjugates by Chemical Conjugation

Conjugates may be formed between heavy chain of Tetanus or Botulinum neurotoxins and CDT using the following methods.

Preparation of Botulinum Heavy Chains by Chemical Methods:

The various serotypes of the clostridial neurotoxins may be prepared and purified from various toxigenic strains of *Clostridium botulinum* and *Clostridium tetani* by methods employing standard protein purification techniques as described previously (Shone and Tranter 1995, Current Topics in Microbiology, 194, 143-160). Samples of botulinum neurotoxin (1 mg/ml) are dialysed against a buffer containing 50 mM Tris-HCl pH 8.0, 1M NaCl and 2.5M urea for at least 4 hours at 4° C. and then made 100 mM with dithiothreitol and incubated for 16 h at 22° C. The cloudy solution which contains precipitated light chain is then centrifuged at 15000×g for 2 minutes and the supernatant fluid containing the heavy chain retained and dialysed against 50 mM Hepes pH 7.5 containing 0.2M NaCl and 5 mM dithiothreitol for at least 4 hours at 4° C. The dialysed heavy chain is centrifuged at 15000×g for 2 minutes and the supernatant retained and dialysed thoroughly against 50 mM Hepes pH 7.5 buffer containing 0.2M NaCl and stored at −70° C. The latter procedure yields heavy chain >95% pure with a free cysteine residue which can be used for chemical coupling purposes.

The heavy chains of the botulinum neurotoxins may also be produced by chromatography on QAE Sephadex as described by the methods in Shone and Tranter (1995) (Current Topics in Microbiology, 194, 143-160; Springer).

Production of CDT-Heavy Chain Constructs by Chemical Methods:

Recombinant CDT subunits may be purified as described in Examples 3 and 4. CDT is chemically modified by treatment with a 25 fold molar excess of N-succinimidyl 3-[2-pyridyldithio] propionate (SPDP) in 0.05M Hepes buffer pH 7.0 containing 0.1M NaCl for 60 min at 22° C. The excess SPDP may be removed by dialysis against the same buffer at 4° C. for 16 h. The substituted CDT is then mixed in a 1:1 molar ratio with heavy chain purified from *Clostridium botulinum* type A neurotoxin purified as described in this Example and incubated at 4° C. for 16 h. During the incubation period CDT may be conjugated to the botulinum heavy chain fragment by free sulphydryl groups. After incubation, the CDT-heavy chain construct can be purified by gel filtration chromatography on Sephadex G200.

Constructs of the invention may also be formed by the above method using polypeptides containing the botulinum heavy chains that have been produced by recombinant technology.

Example 6

Formation of Targeting Moiety (TM)-CDT Conjugates by Recombinant Methods

Conjugates could be formed between the CDT subunits and a targeting moiety using standard cloning techniques. Commercial vectors are available for the production of fusion proteins including pEZZ18 (Amersham-Pharmacia Biotech) which produces an N-terminally ZZ-tagged (IgG binding) protein; pMAL (NEB), producing MBP-tagged proteins; and pET43 (Novagen) which produces NusA tagged proteins.

Conjugates could also be formed by sequential cloning of TM and CDT into a suitable vector to generate "in-frame" gene fusions.

The recombinant proteins could be produced in an expression system which result in addition of peptide tags to facilitate purification (eg. 6 His, S peptide, T7 peptide, calmodulin binding peptide, maltose binding protein).

Incorporation of a protease cleavage site (eg. factor Xa, thrombin, enterokinase) between the peptide tag and the expressed TM-CDT fusion allows this to be removed after purification.

Additionally recombinant conjugates could be produced as described in Michael, N. P. (1996) Immunotechnology 2, pp 47-57, substituting CDT for carboxypeptidase.

Example 7

Monitoring for the Presence of DNase Activity Associated with Conjugates

DNase activity can be monitored in conjugates by incubation of the conjugated CDT-TM with supercoiled plasmid DNA in the presence of 25 mM HEPES, pH7, 4 mM MgCl$_2$ and CaCl$_2$. Plasmid degradation can be monitored by agarose gel electrophoresis, as described in Sambrook et al. 1989, Molecular Cloning a Laboratory Manual, Second Edition, Cold Spring Harbor Laboratory Press, Cold Spring Harbor, N.Y.

As an alternative, DNase I activity may be analysed by the method of Takahashi (1991) Anal. Biochem. 198, pp 246-249. For example, DNase activity can be monitored in conjugates by incubation of the conjugated CDT-TM with supercoiled plasmid DNA in the presence of 25 mM HEPES, pH7, 4 mM MgCl$_2$ and CaCl$_2$. Plasmid degradation can then be monitored by agarose gel electrophoresis.

Example 8

Detection of Cytotoxic Properties Associated with Conjugates

Conjugates can be applied to the cell monolayers in tissue culture dishes. Conjugates are applied and incubated for 18 hours. The medium is then replaced with new medium and the incubation continued for a further 24-48 hours. Cytotoxic events could be detected in a number of ways.

Empirical Determination:

In cell types where cellular distension is evident, examination of the cell monolayer microscopically shows clear evidence of cytotoxic effects (Pérès et al., 1997, Molecular Microbiology 24:1095-1107). Conjugates made with CdtB of *C. jejuni* and the heavy-chain of tetanus toxin were applied to Vero cells. These demonstrated increased levels of cell death and reduced viability of the cell monolayer compared to controls treated with the CdtB, or heavy-chain alone (see Table 1).

FACS Analysis for Determination of DNA Content:

Analysis of DNA content may be used to show if CDT, and conjugates of CDT, have caused a metabolic block in the cell cycle (Camayras et al., 1997, Infection and Immunity, 65: pp 5088-5095).

TABLE 1

Cytotoxic effect of CDT-Dip-Tet conjugates on NG108 cells

| Treatment | Confluence of cell monolayer (%) | Cell morphology |
|---|---|---|
| No treatment | 100 | Normal, neuronal cells |
| CDT | 10-50 | Slightly enlarged cells, highly vacuolated cytoplasm |
| MBP-CdtB | 100 | As controls |
| Dip-Tet | 95 | Approx 40% of cells rounded |
| MBP-CdtB/Dip-Tet conjugates | 20 | Cells sparse, rounded. Some vacuation and blebs observed |

The invention claimed is:

1. An isolated nucleic acid sequence comprising the sequence of SEQ ID NO: 1 and/or SEQ ID NO: 3.

2. An isolated peptide sequence comprising the sequence SEQ ID 2 and/or SEQ ID 4.

3. An agent comprising first and second components, the first component being a targeting moiety (TM) and the second component being a DNase that is a cytolethal distending toxin (CDT), wherein the TM is capable of directing the second component to the target cell of interest, and wherein the DNase causes death to the target cell by a lytic mechanism, wherein the second component comprises SEQ ID 2 and/or SEQ ID 4.

4. A method for preparing an agent according to claim 3 comprising expression of one or more nucleic acid constructs encoding the first and second components, wherein the nucleic acid construct encoding the second component comprises SEQ ID 1 and/or SEQ ID 3.

* * * * *

UNITED STATES PATENT AND TRADEMARK OFFICE
CERTIFICATE OF CORRECTION

| | | |
|---|---|---|
| PATENT NO. | : 7,422,740 B1 | Page 1 of 1 |
| APPLICATION NO. | : 10/129558 | |
| DATED | : September 9, 2008 | |
| INVENTOR(S) | : Purdy et al. | |

It is certified that error appears in the above-identified patent and that said Letters Patent is hereby corrected as shown below:

On the title page,

[*] Notice:    Subject to any disclaimer, the term of this patent is extended or adjusted under 35 USC 154(b) by (310) days Delete the phrase "by 310 days" and insert -- by 858 days --

Signed and Sealed this

Twenty-first Day of July, 2009

JOHN DOLL
*Acting Director of the United States Patent and Trademark Office*